United States Patent
Satoh et al.

(10) Patent No.: US 6,379,507 B1
(45) Date of Patent: Apr. 30, 2002

(54) PROCESS FOR PRODUCING METHYLAL

(75) Inventors: Seinosuke Satoh; Yukio Tanigawa, both of Kurashiki (JP)

(73) Assignee: Asahi Kasei Kabushiki Kaisha, Tokyo (JP)

(*) Notice: Subject to any disclaimer, the term of this patent is extended or adjusted under 35 U.S.C. 154(b) by 0 days.

(21) Appl. No.: 09/365,897

(22) Filed: Aug. 3, 1999

(30) Foreign Application Priority Data

Aug. 3, 1998 (JP) .......................................... 10-229962

(51) Int. Cl.[7] .............................. B01D 3/10; B01D 3/34; C07C 45/82; C07C 45/90
(52) U.S. Cl. .......................... 203/29; 203/20; 203/14; 203/17; 203/41; 203/93; 203/94; 203/96; 203/97; 203/98; 568/493
(58) Field of Search ................................. 203/2, 14, 41, 203/29, 94, 68, 91, 93, 96, 20, DIG. 6, 98, 17, 97; 568/449, 493, 492, 594; 422/188–190, 211

(56) References Cited

U.S. PATENT DOCUMENTS

| | | | | |
|---|---|---|---|---|
| 4,385,965 A | * | 5/1983 | Miller et al. | ................... 203/75 |
| 4,967,014 A | | 10/1990 | Masamoto et al. | |
| 5,108,550 A | | 4/1992 | Pinaire et al. | |
| 5,291,989 A | | 3/1994 | Pinaire et al. | |
| 5,447,609 A | | 9/1995 | Yeoman et al. | |
| 5,498,318 A | | 3/1996 | Alagy et al. | |
| 6,015,875 A | * | 1/2000 | Smith, Jr. et al. | ............ 528/501 |
| 6,160,185 A | * | 12/2000 | Tanaka et al. | ................ 568/594 |

FOREIGN PATENT DOCUMENTS

| | | |
|---|---|---|
| JP | 4015005 | 7/1940 |
| JP | B2415213 | 3/1992 |

OTHER PUBLICATIONS

English Abstract of Japanese Patent No. 40–15005.

* cited by examiner

*Primary Examiner*—Virginia Manoharan
(74) *Attorney, Agent, or Firm*—Birch, Stewart, Kolasch & Birch, LLP

(57) ABSTRACT

A process for producing methylal that involves feeding a liquid containing methanol, formaldehyde and water to an uppermost reactor of at least four solid acid catalyst-filled reactors which are each externally connected to an intermediate portion of a distillation column; and forcibly circulating a liquid containing methanol, formaldehyde, water and produced methylal in a temperature range of 80° C. to 100° C. between the distillation column and each reactor connected to the distillation column below said uppermost reactor, whereby the vapor in the distillation column, which vapor has been subjected to vapor-liquid contact with the liquid containing methanol, formaldehyde, water and produced methylal and which liquid has been subjected to solid-liquid contact in a lowermost reactor of the reactors connected to the intermediate portion of the distillation column, is successively subjected to vapor-liquid contact with the liquids containing methanol, formaldehyde, water and produced methylal circulated between the distillation column and each reactor connected to the distillation column above said lowermost reactor in which the above vapor phase is successively increased.

16 Claims, 1 Drawing Sheet

PROCESS FOR PRODUCING METHYLAL

BACKGROUND OF THE INVENTION

1. Field of the Invention

This invention relates to a process for producing methylal which is utilized as a plasticizer for a resin, an analgesic, a perfume or the like. More particularly, this invention relates to a process for producing methylal with good efficiency from methanol and formaldehyde using a solid acid as a catalyst.

2. Description of Related Art

Methylal is synthesized by condensation reaction of methanol with formaldehyde or paraformaldehyde in the presence of an acidic catalyst. As a method for the synthesis of methylal, it is generally known to use an acidic catalyst such as hydrochloric acid, ferric chloride or zinc chloride. Moreover, in JP-B-40-15,005, a method is proposed by which the starting mixture of methanol with aqueous formalin solution is passed through a distillation column packed with a cation exchanger to enhance the reaction yield of methylal. Furthermore, in each of the specifications of U.S. Pat. Nos. 5,108,550, 5,291,989 and 5,498,318, a reaction system in which a catalyst-packed type distillation column is used is disclosed as a method of enhancing the reaction yield though it is not limited to the synthesis of methylal. Further, in U.S. Pat. No. 4,967,014, there is disclosed a method for efficiently synthesizing methylal by a reaction-distillation column system in which a liquid consisting of methanol, formaldehyde and water is forcibly circulated to a solid acid catalyst-containing reactor connected to a distillation column.

However, according to the method which has heretofore been proposed, such problems are caused in some cases that when methylal is synthesized from methanol and formaldehyde, the reaction yield is restricted by water produced as a by-product and that the production has to be discontinued when the catalyst ability is lowered. The productivity can be greatly restricted because of the treatment of the waste water produced as a by-product, and in some cases, the industrial practice has been accompanied by much complexity.

For example, the reaction where methylal is synthesized from methanol and formaldehyde using an acidic catalyst such as hydrochloric acid is an equilibrium reaction, so that in said reaction, the enhancement of reaction yield has been restricted by the presence of water produced as a by-product as shown by the following reaction formula:

$$2CH_3OH + CH_2O \leftrightarrows CH_3OCH_2OCH_3 + H_2O.$$

Moreover, as a method of enhancing the reaction yield, JP-B-40-15,005 proposes that the starting mixture of methanol with aqueous formalin solution is previously subjected to acetalization using a cation exchanger and a part of the liquid flowing out of the reaction chamber in which the cation exchanger is used is fed again from a position above the place where the starting mixture is fed. However, when an ion exchange resin has been used over a long period of time, such problems have been caused in some cases that the particles of the resin are collapsed into fine powder and the catalyst ability is lowered by metal ion-substitution or the like. In the method of said Japanese publication, such a system is inconvenient since the distillation column is packed with a cation exchanger, and the production of methylal must be discontinued every time the catalyst ability is lowered.

Moreover, in U.S. Pat. No. 4,967,014, there is proposed such a method that methylal is synthesized by a reaction-distillation column system in which a liquid consisting of methanol, formaldehyde and water is forcibly circulated to a solid acid catalyst-containing reactor connected to the distillation column. In the method of said patent publication, the reaction yield is enhanced and, in addition thereto, since the reactor uses an external, forcible circulation system, the installation of a preliminary reactor enables the regeneration, exchange and withdrawal of the catalyst to be conducted in the preliminary reactor, whereby a long term continuous operation is made possible without discontinuing the methylal production. However, while the method of said patent publication is excellent for the efficient production of methylal, when treatment of the by-product water is taken into consideration, the concentrations of formaldehyde and methanol in the distillation column bottom product become high and a high-COD load waste water is generated. At the same time, in the continuous operation of the distillation column, a pressure rise due to bubbling in the distillation column is caused, and hence, an inconvenience has been caused in carrying out the industrial production of methylal.

SUMMARY OF THE INVENTION

The present inventors have extensively examined a method for the industrial production of methylal to find the usefulness of a solid acid catalyst and simultaneously have found the optimum conditions for the distillation column.

According to this invention, there is provided a process for producing methylal by contacting a liquid containing methanol, formaldehyde and water with a solid acid catalyst to obtain a component rich in methylal as a distillate, which process comprises feeding a liquid containing methanol, formaldehyde and water to the upper-most reactor of at least four solid acid catalyst-filled reactors which are each externally connected near to the intermediate portion of a distillation column; forcibly circulating a liquid containing methanol, formaldehyde, water and produced methylal in the temperature range of 80° C. to 100° C. between the distillation column and each of the other reactors which are connected to the lower side of the distillation column, whereby the vapor in the distillation column, which vapor has been subjected to vapor-liquid contact with the liquid containing methanol, formaldehyde, water and produced methylal and which liquid has been subjected to solid-liquid contact in any reactor connected to the lower portion of the distillation column, is successively subjected to vapor-liquid contact with the liquids containing methanol, formaldehyde, water and produced methylal circulated between the distillation column and the remaining reactors which are connected to the distillation column above the reactor in which the above vapor is generated, by which the methylal concentration in the vapor phase is successively increased; simultaneously therewith adding a defoaming agent from the top portion of the distillation column; adjusting the temperature of the bottom product of the distillation column to 100° C. to 130° C.; and withdrawing water produced as a by-product as waste water.

According to the production process of this invention, the synthesis of methylal in the prior art in which the reaction yield has been restricted by water produced as a by-product can be carried out in high yields. The process of this invention facilitates the treatment of water produced as a by-product, further enables continuous production to be achieved by addition of a defoaming agent, and hence, is very high in industrial value.

DESCRIPTION OF THE PREFERRED EMBODIMENTS

Figure 1:
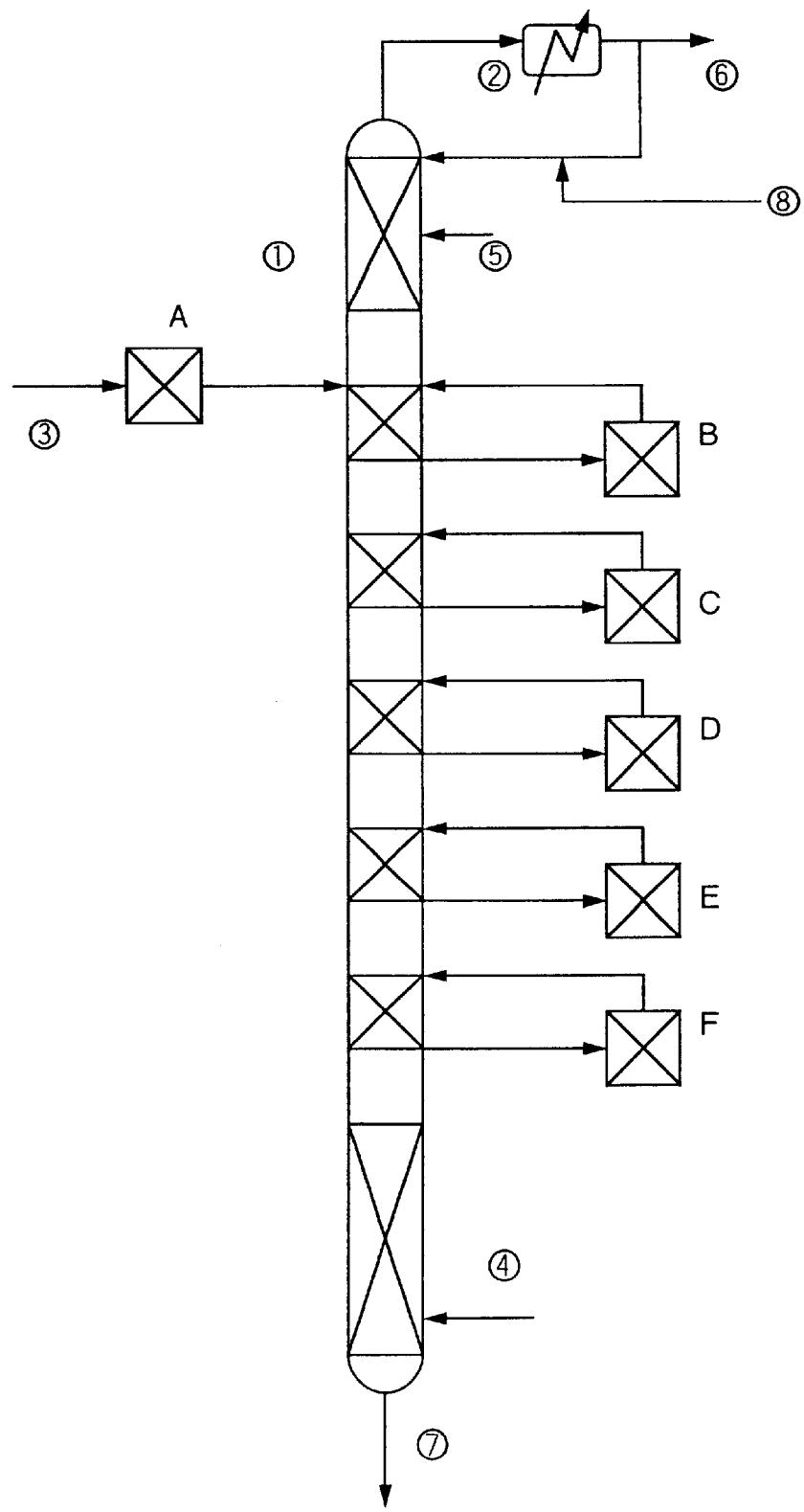
FIG. 1 is a schematic diagram of a distillation column which has reactors externally connected near thereto and which is used in this invention.

The nature of the solid acid catalyst-filled reactors used in this invention and the manner in which a liquid containing methanol, formaldehyde, methylal and water which has been subjected to solid-liquid contact with the solid acid catalyst is subjected to vapor-liquid contact with a vapor containing methylal are not critical. However, an example thereof is shown in FIG. 1.

This invention is explained below taking as an example the case where the distillation column shown in FIG. 1 is used.

In FIG. 1, 1 refers to a distillation column, 2 to a condenser, 3 to a feeding line through which a liquid containing methanol, formaldehyde and water is fed, A to F to reactors filled with a solid acid catalyst, 4 to a steam-feeding line, 5 to an aqueous formalin solution-feeding or water-feeding line, 6 to a distillate, 7 to the bottom product of the column bottom and 8 to a defoaming agent-feeding line.

The distillation column used in this invention is not critical, and may be either a plate column or packed column, which includes, for example, a bubble cap type, a valve tray type, a sheave tray type and the like. Moreover, as the packings, there can be adopted those of various forms such as Raschig ring, Paul ring, Dickson ring, tellerlette and the like. Moreover, the materials to be used for the distillation column are not critical; however, materials having corrosion resistance at least corresponding to SUS304 are preferably used because formic acid is generated, though in slight amount, by the oxidation of formaldehyde.

In this invention, to the intermediate portion of the distillation column 1 are externally connected the solid acid catalyst-filled reactors A to F. Methanol and aqueous formalin solution which are the starting materials in this invention are first of all fed through the feeding line 3 to the uppermost reactor A, and thereafter fed to the distillation column 1. In this invention, a liquid containing methanol, aqueous formalin solution and water is forcibly circulated between the distillation column and each of the solid acid catalyst-filled reactors B to F externally connected to the distillation column 1 to synthesize methylal, and the methylal produced is returned to the distillation column 1. On the other hand, the vapor in the distillation column in which the vapor from the distillation column bottom is subjected to vapor-liquid contact with the liquid containing methanol, formaldehyde, water and the produced methylal which liquid has been subjected to solid-liquid contact in any reactor connected to the lower portion of the distillation column, is successively subjected to vapor-liquid contact with the liquids containing methanol, formaldehyde, water and produced methylal which had been circulated and subjected to solid-liquid contact in the reactors above the lowermost reactor. By the above procedure, the methylal concentration in the vapor phase is successively increased. By this process, methylal can be obtained in a high yield.

Moreover, the number of plates between the distillation column portion to which the uppermost reactor A is connected and the distillation column top is preferably not less than 5, more preferably 10 to 20. When the number of plates between the distillation column portion to which the uppermost reactor A is connected and the distillation column top is less than 5, the methanol concentration in the top distillate becomes high and the purity of methylal in the distillate obtained becomes unsatisfactory.

Furthermore, the number of plates between the distillation column portion to which the lowermost reactor F is connected and the distillation column bottom is preferably not less than 5, more preferably not less than 15. When the number of plates between the distillation column portion to which the lowermost reactor F is connected and the distillation column bottom is less than 5, methanol is incorporated into the bottom product of the column bottom, a loss is caused corresponding thereto, and simultaneously the COD load in the waste water becomes high.

The condensate obtained from the distillation column top is divided into a reflux to be returned to the column top and a distillate. However, the ratio of the reflux to be returned to the column top to the distillate (mole ratio) is preferably from 5:1 to 1:2.

The operation of the distillation column in this invention is usually effected at normal pressure, though it is preferable to effect the operation at a pressure in the range of 1 atm to 2 atm. Moreover, when the distillation is carried out at this operation pressure, it is important that when the five forcible circulation reactors B to F which are connected to the distillation column and in which the liquid is to be forcibly circulated are operated, the temperatures of the respective liquids to be circulated in the forcible circulation reactors B to F are adjusted, respectively, to 80 to 90° C., 85 to 95° C., 85 to 95° C., 90 to 100° C. and 90 to 100° C. and the temperature of the bottom product of the distillation column is adjusted to at least 100° C. By adjusting the temperatures of the portions of the distillation column to which the five reactors B to F, in which the liquids are forcibly circulated, are connected and the temperature of the bottom portion of the distillation column to the above-mentioned temperatures, the compositions of methanol and produced methylal stabilize and the composition of the bottom product of the column bottom containing water produced as a by-product becomes 0.1% or less of formaldehyde and 0.01% or less of methanol, and it is possible to treat the bottom product as a low COD load waste water in which the COD load is 500 ppm or less.

This invention has been explained above referring to the case of the use of six reactors filled with a solid acid catalyst as an example. However, in this invention, the number of the reactors is at least 4, preferably at least 6. When the number of the reactors is less than 4, the reaction for synthesizing methylal becomes insufficient, and the formaldehyde concentration in the waste liquid from the distillation column bottom becomes high and the COD load becomes large, so that the use of less than four reactors is not desirable.

As the solid acid catalyst with which the reactors are to be filled, any known solid acid catalyst may be used, and there are mentioned cation exchange resins, fluorinated alkaline resin sulfonic acid group derivatives, crystalline zeolite and the like as examples. As the cation exchange resin, either carboxyl group derivatives or sulfonic acid group derivatives can be used; however, sulfonic acid group derivatives are preferred because the reaction yield is higher. Moreover, as the type of ion exchange resin, there can be used either a gel-type cation exchange resin or a macro-reticular cation exchange resin. However, a macro-reticular cation exchange resin is preferred in view of the high reaction yield. As the fluorinated alkaline resin sulfonic acid group derivatives, tetrafluoroethylene resin sulfonic acid group derivatives are preferable. Moreover, as the crystalline zeolite (crystalline aluminosilicate), silica zeolite whose $SiO_2/Al_2O_3$ mole ratio is at least 10 is preferred.

Furthermore, the amount of the solid acid catalyst with which the reactors are to be filled is preferably 0.2 to 1 part by weight per part by weight of methylal vapor distilled out per hour from the distillation column top. When the amount of the catalyst with which the reactor is filled is smaller than the above-mentioned amount, the reaction becomes insufficient and the COD load of the waste water from the distillation column bottom becomes higher.

In this invention, the amount of the liquid to be forcibly circulated in each of the five solid acid catalyst-filled reactors B, C, D, E and F externally connected to the distillation column 1 is determined depending upon the catalyst ability and amount of the solid acid catalyst; however, it is preferable to control the amount of the liquid circulated in each of the reactors to 15 to 30 parts by weight per part by weight of methylal vapor distilled out of the distillation column top.

In addition, the composition of the reaction liquid to be circulated in each of the forcible circulation reactors connected to the distillation column below the uppermost reactor is 25 to 35 parts by weight of methanol, 0.005 to 5 parts by weight of formaldehyde, 55 to 75 parts by weight of water and 0.01 to 5 parts by weight of methylal. By increasing the methanol concentration as mentioned above, it is possible to complete the reaction and decrease the formaldehyde concentration in the distillation column bottom, whereby the COD load of the waste water from the distillation column bottom can be decreased.

Methanol and aqueous formalin solution which are the starting materials in this invention are first of all fed through the feeding line 3 to the uppermost reactor A, and thereafter fed to the distillation column 1. Moreover, in this invention, water or aqueous formalin solution is fed to the distillation column from a position above the uppermost reactor A through the feeding line 5. The water or aqueous formalin solution fed from a position above the uppermost reactor A is subjected to vapor-liquid contact with the vapor containing methylal and methanol which vapor goes up in the distillation column, and 98% or more of methylal and 1% or less of methanol are distilled out of the column top. The feeding position is, when the number of plates between the distillation column portion to which the uppermost reactor A is connected and the column top is 15 to 20, preferably a position in the number-of-plate range of 10 to 15 counting from the distillation column portion to which the uppermost reactor A is connected.

The amount of methanol fed is 2.0 to 2.2 moles per mole of formaldehyde. When the amount is less than 2.0 moles per mole of formaldehyde, formaldehyde becomes stoichiometrically in excess and becomes discharged from the distillation column bottom, whereby the formaldehyde concentration in the waste liquid becomes high and the COD load becomes large. This is not desirable.

Moreover, in this invention, a defoaming agent is added to the top portion of the distillation column. When no defoaming agent is added, bubbling is caused in the distillation column, the pressure in the distillation column rises and continuous stable operation becomes impossible. This is not desirable. As a method of adding a defoaming agent, there are mentioned a method of adding it to the reflux, a method of directly adding it to the distillation column, and the like, and any of these methods can be used.

The amount of the defoaming agent added is 0.001 ppm to 1,000 ppm, preferably 0.01 ppm to 100 ppm, based on the amount of methylal vapor distilled out of the top portion of the distillation column.

As the defoaming agent, a conventional defoaming agent can be used and the kind thereof is not critical. However, the preferable defoaming agent in this invention is silicone oil.

As the silicone oil, there are mentioned general dimethyl type silicone oil, modified type silicone oil, solution type silicone oil and emulsion type silicone oil. The modified type silicone oil is preferred, and polyether-modified silicone oil is particularly preferable. It is sufficient that the viscosity of silicone oil is 50 to 100,000 centipoises and it is preferable to use a polyether-modified silicone oil having a viscosity of 100 to 2,000 centipoises.

Examples are shown below to explain this invention, but this invention is not restricted thereby at all.

EXAMPLE 1

The distillation column having 6 reactors as shown in FIG. 1 was used. The number of plates between the distillation column portion to which the uppermost reactor A was connected and the distillation column top was 15 and the number of plates between the distillation column portion to which the lowermost reactor F was connected and the distillation column bottom was 15. Each of the reactors A, B, C, D, E and F was filled with 500 g of a macro-reticular, strongly acidic, cation exchange resin (trade name: Amberlist 35). Through the feeding line 3, 45% aqueous formalin solution was fed at a rate of 560 g/h and methanol at a rate of 580 g/h. In the intermediate portion of the distillation column, there were provided liquid component-withdrawing plates and the reaction liquids were circulated to the reactors B, C, D, E and F at a rate of 40 liters/h by pumps to subject them to solid-liquid contact with the catalyst in the reactors. The reaction liquids containing methylal which left the reactors B, C, D, E and F were subjected to vapor-liquid contact with the vapor which went up in the distillation column from its bottom to its top to increase the methylal concentration.

Moreover, 20% aqueous formalin solution was fed at a rate of 100 g/h through the feeding line 5 to allow the aqueous formalin solution to selectively absorb methanol from the methylal-methanol azeotropic mixture. Further, a polyether-modified silicone oil having a viscosity of 750 centipoises was diluted with methylal so that its amount became 0.01 g/h when the amount of gas was 2,100 g/h in the distillation column top portion and fed to the reflux line of the distillation column. Methylal synthesis was conducted under the conditions that the pressure of the distillation column was 1.2 atm and the mole ratio of the reflux returned to the column top to the distillate distilled out was 2:1. The temperatures of the reactors B, C, D, E and F were 85° C., 91° C., 94° C., 95° C. and 95° C., respectively, when the operation of the distillation column stabilized after 75 hours. Moreover, the temperature of the distillation column top was 47° C., and the temperature of the distillation column bottom was 112° C. The composition of the liquid circulated in each reactor was such that the respective concentrations of formal-dehyde, water, methanol and methylal were 3.1%, 61.7%, 32.0% and 3.2% in the reactor B; 1.3%, 67.5%, 30.2% and 1.0% in the reactor C; 0.5%, 70.2%, 28.9% and 0.4% in the reactor D; 0.2%, 71.5%, 28.2% and 0.1% in the reactor E; and 0.08%, 72.6%, 27.3% and 0.02% in the reactor F; and a distillate was taken out at a rate of 702 g/h from the column top. The composition of the distillate was 98% of methylal, 0.3% of methanol and 1.2% of water. The composition of the bottom product 7 withdrawn from the column bottom was 0.06% of formaldehyde and 0.001% of methanol. The reaction yield based on the formaldehyde was 99.9%. Furthermore, when the continuous operation was conducted for 1,000 hours, the operation of distillation and the like stabilized, and the flow rates and compositions of the distillate and the bottom product after 1,000 hours stabilized.

EXAMPLES 2 to 4

The same procedure as in Example 1 was repeated, except that various solid acids were used as the solid acid catalyst in place of the macro-reticular, strongly acidic cation exchange resin. The results obtained are shown in Table 1.

Comparative Example 1

The same procedure as in Example 1 was repeated, except that the Reactors D, E and F were removed from the distillation column. A distillate was taken out at a rate of 680 g/h from the column top. The composition of the distillate was 98% of methylal, 0.8% of methanol and 1.2% of water. The composition of the bottom product 7 withdrawn from the column bottom was 0.6% of formaldehyde and 1.3% of methanol. This bottom product was clearly higher in COD load than in the Examples and had a severe problem of treating the waste water from the viewpoint of industrial production.

Comparative Example 2

The same procedure as in Example 1 was repeated, except that the number of plates between the distillation column portion to which the uppermost reactor A was connected and the distillation column top was changed from 15 to 3 and the number of plates between the distillation column portion to which the lowermost reactor F was connected and the distillation column bottom was changed from 15 to 3. A distillate was taken out at a rate of 690 g/h from the column top. The composition of the distillate was 94.3% of methylal, 4.5% of methanol and 1.2% of water. The composition of the bottom product 7 withdrawn from the column bottom was 0.8% of formaldehyde and 2.5% of methanol. The distillate was inferior in methylal purity, and the bottom product was clearly higher in COD load than in the Examples and had a severe problem of treating waste water from the viewpoint of industrial production.

Comparative Example 3

In the same manner as in Example 1, except that the temperature of the reactor F was elevated to 79° C., the synthesis of methylal was conducted. The temperatures of the reactors B, C, D and E were 67° C., 73° C., 75° C. and 77° C., respectively, when the operation of the distillation column stabilized. The composition of the distillate was 98% of methylal, 0.9% of methanol and 0.9% of water. The composition of the bottom product 7 withdrawn from the column bottom contained 1.3% of formaldehyde and 0.3% of methanol.

Comparative Example 4

In the same manner as in Example 1, except that the temperature of the bottom product in the distillation column bottom was elevated to 98° C., the synthesis of methylal was conducted. The composition of the distillate was 98% of methylal, 1.0% of methanol and 1.0% of water. The composition of the bottom product 7 withdrawn from the column bottom contained 1.5% of formaldehyde and 1.5% of methanol.

Comparative Example 5

In the same manner as in Example 1, except that the feeding of a polyether-modified silicone oil added to the reflux line of the distillation column was canceled, the synthesis of methylal was conducted. From 60 hours after the initiation of operation, bubbling was gradually confirmed in the distillation column, and the temperature of the distillation column bottom portion further rose to 115° C. When the temperature of the column bottom portion finally became 120° C., the operation was terminated. At this time, bubbling was confirmed in the whole of the distillation column.

TABLE 1

| Example No. | Solid acid | Column top distillate | | | Liquid withdrawn from column bottom | | |
| --- | --- | --- | --- | --- | --- | --- | --- |
| | | Distillation rate (g/h) | Methylal (%) | Methanol (%) | Withdrawal rate (g/h) | Formaldehyde (%) | Methanol (%) |
| 2 | Cation exchange resin (Gel type) Amberlite 120B | 705 | 98 | 0.4 | 1008 | 0.08 | 0.002 |
| 3 | Crystalline zeolite (Silica/alumina mole ratio = 10) | 700 | 98 | 0.4 | 1006 | 0.07 | 0.001 |
| 4 | Tetrafluoro- ethylene resin sulfonic acid group derivative (Nafion H) | 705 | 98 | 0.4 | 1010 | 0.07 | 0.001 |

What is claimed is:

1. A process for producing methylal by contacting a liquid containing methanol, formaldehyde and water with a solid acid catalyst to obtain a component rich in methylal as a distillate, which process comprises feeding a liquid containing methanol, formaldehyde and water to an uppermost reactor of at least four solid acid catalyst-filled reactors which are each externally connected to an intermediate portion of a distillation column;

forcibly circulating a liquid containing methanol, formaldehyde, water and produced methylal in a temperature range of 80° C. to 100° C. between the distillation column and each reactor connected to the distillation column below said uppermost reactor, whereby the vapor in the distillation column, which vapor has been subjected to vapor-liquid contact with the liquid containing methanol, formaldehyde, water and produced methylal and which liquid has been subjected to solid-liquid contact in a lowermost reactor of the reactors connected to the intermediate portion of the distillation column, is successively subjected to vapor-liquid contact with the liquids containing methanol, formaldehyde, water and produced methylal circulated between the distillation column and each reactor connected to the distillation column above said lowermost reactor in which the above vapor phase is successively increased;

simultaneously therewith adding a defoaming agent from a top portion of the distillation column and adjusting the temperature of the bottom product of the distillation column to 100° C. to 130° C.; and withdrawing water produced as a by-product as waste water.

2. The process according to claim 1, wherein at least 6 solid acid catalyst-filled reactors are present.

3. The process according to claim 1, wherein the solid acid catalyst with which the reactors are filled is selected from the group consisting of cation exchange resins, fluorinated alkaline resin sulfonic acid group derivatives and crystalline zeolite.

4. The process according to claim 1, wherein the number of the forcible circulation reactors connected to the intermediate portion of the distillation column below the uppermost reactor is 5 and the temperatures of the liquids to be circulated in the above reactors are, in the order from the upper side of the distillation column, 80 to 90° C., 85 to 95° C., 85 to 95° C., 90 to 100° C. and 90 to 100° C.

5. The process according to claim 1 or 4, wherein the composition of each of the reaction liquids which are circulated in the forcible circulation reactors connected to the distillation column below the uppermost reactor is 25 to 35 parts by weight of methanol, 0.005 to 5 parts by weight of formaldehyde, 55 to 75 parts by weight of water and 0.01 to 5 parts by weight of methylal.

6. The process according to claim 1, wherein methanol is fed to the distillation column in an amount of 2.0 to 2.2 moles per mole of formaldehyde.

7. The process according to claim 1 or 4, wherein the operation pressure of the distillation column to which the reactors are externally connected is 1 to 2 atm.

8. The process according to claim 1 or 4, wherein the amount of the liquid circulated in each of the reactors connected to the distillation column below the uppermost reactor is 15 to 30 parts by weight per part by weight of the methylal vapor distilled out of the top of the distillation column.

9. The process according to claim 2, wherein the amount of the solid acid catalyst used per one reactor is 0.2 to 1 part by weight per part by weight of methylal vapor distilled out per hour from the top of the distillation column.

10. The process according to claim 1, wherein 10 to 20 plates of the distillation column are present between the portion to which the uppermost reactor is connected and the distillation column top, and at least 15 plates of the distillation column are present between the portion to which the lowermost reactor is connected and the distillation column bottom.

11. The process according to claim 1, wherein methylal vapor produced out of the top of the distillation column is condensed to produce a methylal distillate, wherein a portion of the methylal distillate is returned to the top of the distillation column, wherein a mole ratio of the methylal distillate returned to the column top to the produced methylal distillate is between 5:1 and 1:2.

12. The process according to any one of claims 3, 4 and 6, further comprising feeding water or aqueous formalin solution to the distillation column at a position above said uppermost reactor wherein the composition of distillate obtained from the column top by subjecting said water or aqueous formalin solution with the vapor containing methylal and methanol which goes up in the distillation column is not less that 98% of methylal and not more than 1.0% of methanol, and the composition of the bottom product from the column bottom is not more than 0.1% of formaldehyde and not more than 0.01% of methanol.

13. The process according to claim 1, wherein the amount of the defoaming agent added is 0.01 ppm to 100 ppm based on methylal vapor distilled out of the top portion of the distillation column.

14. The process according to claim 1 or 13, wherein the defoaming agent is silicone oil.

15. The process according to claim 14, wherein the silicone oil is a polyether-modified silicone oil.

16. The process according to claim 14, wherein the silicone oil has a viscosity of 100 to 20,000 centipoises.

* * * * *